(12) United States Patent
Mechoulam et al.

(10) Patent No.: US 11,058,652 B2
(45) Date of Patent: Jul. 13, 2021

(54) METHODS FOR TREATMENT OF PRADER-WILLI SYNDROME

(71) Applicant: Yissum Research Development Company of the Hebrew University of Jerusalem Ltd., Jerusalem (IL)

(72) Inventors: Raphael Mechoulam, Jerusalem (IL); Joseph Tam, Jerusalem (IL); Reem Smoum, Jerusalem (IL); Saja Baraghithy, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 16/092,714

(22) PCT Filed: Apr. 13, 2017

(86) PCT No.: PCT/IL2017/050447
§ 371 (c)(1),
(2) Date: Oct. 10, 2018

(87) PCT Pub. No.: WO2017/179058
PCT Pub. Date: Oct. 19, 2017

(65) Prior Publication Data
US 2019/0151264 A1 May 23, 2019

Related U.S. Application Data

(60) Provisional application No. 62/322,555, filed on Apr. 14, 2016.

(51) Int. Cl.
| | | |
|---|---|---|
| *A61K 31/19* | (2006.01) | |
| *A61K 31/197* | (2006.01) | |
| *A61P 43/00* | (2006.01) | |
| *A61P 19/10* | (2006.01) | |
| *A61K 45/06* | (2006.01) | |

(52) U.S. Cl.
CPC ............ *A61K 31/19* (2013.01); *A61K 31/197* (2013.01); *A61K 45/06* (2013.01); *A61P 19/10* (2018.01); *A61P 43/00* (2018.01)

(58) Field of Classification Search
CPC ............................ C07C 2101/14; A61K 31/19
See application file for complete search history.

(56) References Cited

FOREIGN PATENT DOCUMENTS

| EP | 1867994 A2 | 12/2007 |
| WO | 2005073164 A1 | 8/2005 |
| WO | 2009125409 A2 | 10/2009 |
| WO | WO2009/125409 | * 10/2009 |

OTHER PUBLICATIONS

Eriksen et al., Bone, 2014, 58:126-35(abstract).*
International Preliminary Report on Patentability received in PCT Application No. PCT/IL2017/050447, dated Oct. 16, 2018.
Smoum et al., Oleoyl serine, an endogenous N-acyl amide, modulates bone remodeling and mass. PNAS, 107(41), pp. 17710-17715, (2010).
Jan et al., Novel effect of N-palmitoyl-L-serine phosphoric acid on cytosolic Ca2+ levels in human osteoblasts. Pharmacology & Toxicology, 93, pp. 71-76. (2003).
International Search Report and Written Opinion received in PCT Application No. PCT/IL2017/050447, dated Jul. 24, 2017.
"Osteoporosis Evaluation and Therapy in Prader-Willi Syndrome," Consensus Statement of the PWSA (USA) Clinical Advisory Board. The Gathered View (ISSN 1077-9965).
Baraghithy, Saja et al. "Magel2 Modulates Bone Remodeling and Mass in Prader-Willi Syndrome by Affecting Oleoyl Serine Levels and Activity," Journal of Bone and Mineral Research (2018) 1-13.
Bradshaw, Heather B., et al. "Levels of bioactive lipids in cooking oils: olive oil is the richest source of oleoyl serine," J Basic Clin Physiol Pharmacol 2016; 27(3): 247-252.
Kennel, Kurt et al., "Adverse Effects of Bisphosphonates: Implications for Osteoporosis Management," Concise Review for Clinicians. Mayo Clinc Proc. Jul. 2009;84(7):632-638.
Bakker et al., "Bone mineral density in children and adolescents with Prader-Willi syndrome: a longitudinal study during puberty and 9 years of growth hormone treatment", J Clin Endocrinol Metab, 2015, 100(4), 1609-18.
Brunetti et al., Analysis of circulating mediators of bone remodeling in Prader-Willi syndrome. Calcif Tissue Int, 2018, 102(6), 635-643.
Butler et al., Decreased bone mineral density in Prader Willi syndrome: comparison with obese subjects, Am J Med Genet., 2001, 103(3), 216-222.
Donze et al., "Bone mineral density in young adults with Prader-Willi syndrome: a randomized, placebo-controlled, crossover GH trial", Clin Endocrinol (Oxf), 2018, 88(6), 806-812.
Duran et al., "Association between physical activity and bone in children with Prader-Willi syndrome", J Pediatr Endocrinol Metab, 2016, 29(7), 819-26.
Fountain et al, "Prader Willi syndrome and Schaaf-Yang syndrome: neurodevelopmental diseases intersecting at the MAGEL2 gene", Diseases, 2016, 4(1).
Khare et al., "Effect of genetic subtypes and growth hormone treatment on bone mineral density in Prader-Willi syndrome", J Pediatr Endocrinol Metab, 2014, 27(5-6), 511-8.
Khor et al., "Prader-Willi critical region, a non-translated, imprinted central regulator of bone mass: possible role in skeletal abnormalities in Prader-Willi syndrome", PLoS One, 2016, 11(1), e0148155.
Nakamura et al., "Growth hormone treatment for osteoporosis in patients with scoliosis of Prader-Willi syndrome", J Orthop Sci, 2014, 19(6), 877-82.

(Continued)

*Primary Examiner* — Rei Tsang Shiao
(74) *Attorney, Agent, or Firm* — Knobbe, Martens, Olson & Bear LLP

(57) ABSTRACT

The present disclosure provides pharmaceutical compositions comprising a fatty acid amide of an amino acid as defined herein, such as oleoyl-α-methyl-serine, or a stereoisomer or salt thereof, for improving, as in increasing or preventing loss of, bone mineral density and/or treating osteoporosis in patients suffering from Prader-Willi syndrome; and their methods of use.

16 Claims, 5 Drawing Sheets

(56) References Cited

OTHER PUBLICATIONS

Van Nieuwpoort et al., "Body composition, adipokines, bone mineral density and bone remodeling markers in relation to IGF-1 levels in adults with Prader-Willi Syndrome", Int J Pediatr Endocrinol, 2018, 1 (2018).

Viardot et al., "Relative contributions of lean and fat mass to bone mineral density: insight from Prader-Willi syndrome", Front Endocrinol (Lausanne), 2018, 9, 480.

Khoshhal, Khalid I. "Childhood osteoporosis." Journal of Taibah University Medical Sciences 6(2) (2011): 61-76.

* cited by examiner

Wild-type    Magel2⁻/⁻

Length (mm)    15.05±0.13    13.45±0.33*

Wild-type    Magel2⁻/⁻

BV/TV (%)    3.00±0.24    1.53±0.13*

METHODS FOR TREATMENT OF PRADER-WILLI SYNDROME

CROSS REFERENCE TO RELATED APPLICATIONS

This application is the U.S. National Phase under 35 U.S.C. § 371 of International Application No. PCT/IL2017/050447 filed Apr. 13, 2017, designating the U.S. and published as WO 2017/179058 on Oct. 19, 2017, which claims the benefit of U.S. Provisional Patent Application No. 62/322,555 filed Apr. 14, 2016. Any and all applications for which a foreign or domestic priority claim is identified above and/or in the Application Data Sheet as filed with the present application are hereby incorporated by reference under 37 CFR 1.57.

TECHNICAL FIELD

The present invention relates to methods and pharmaceutical compositions for improving bone mineral density and/or treating osteoporosis in patients suffering from Prader-Willi syndrome.

BACKGROUND ART

Bone diseases are disorders and conditions that cause abnormal development and/or impairment in normal bone development. This can result in weakened bones, e.g., due to excessive loss in bone strength and density. Nutrient deficiencies such as a lack of vitamin D or C, hormonal imbalances, and cell abnormalities can cause bone disorders in both children and adults.

Bone is a dynamic connective tissue that includes functionally distinct cell populations required to support the structural, mechanical and biochemical integrity of bone and the human body's mineral homeostasis. The principal cell types involved include osteoblasts responsible for bone formation and maintaining bone mass, osteoclasts responsible for bone resorption, and osteocytes which are thought to be mechanosensor cells that control the activity of osteoblasts and osteoclasts. Osteoblasts and osteoclasts function in a dynamic process termed bone remodeling. The development and proliferation of these cells from their progenitors is governed by networks of growth factors and cytokines produced in the bone microenvironment as well as by systemic hormones. Bone remodeling is ongoing throughout the lifetime of the individual and is necessary for the maintenance of healthy bone tissue and mineral homeostasis. The process remains largely in equilibrium and is governed by a complex interplay of systemic hormones, peptides and downstream signaling pathway proteins, local transcription factors, cytokines, growth factors and matrix remodeling genes.

An interference or imbalance arising in the bone remodeling process can produce bone disease, with the most common bone disorders characterized by a net decrease in bone mass. A primary cause of this reduction in bone mass is an increase in osteoclast number and/or activity.

Prader-Willi syndrome (PWS) is a complex genetic disorder that affects many parts of the body. PWS is caused by the loss of genes in a specific region of chromosome 15. PWS occurs when the region of the paternal chromosome 15 containing these genes is missing. People with PWS typically have mild to moderate intellectual impairment and learning disabilities, short stature, small hands and feet, and morbid obesity. Additionally, patients with PWS suffer from an array of skeletal features that include scoliosis (Holm and Laurnen, 1981), hip dysplasia (West and Ballock, 2004), lower limb alignment abnormalities (Kroonen et al., 2006), reduced bone mineral density (BMD), and an increased risk of bone fractures secondary to osteoporosis (Butler et al., 2001; Vestergaard et al., 2004). Osteoporosis is characterized by the loss of bone and deterioration of the trabecular architecture, which results in bones being more susceptible to fracture.

BMD is affected by the equilibrium between bone formation and bone resorption. In fact, adequate mineral acquisition during childhood is important for peak BMD in late adolescence, and therefore, decreased BMD has a key role in the development of osteoporosis and increased fracture risk later in life. Whether the reduced BMD in PWS is mediated by impaired growth hormone secretion (Bakker et al., 2015; Carrel et al., 2010; de Lind van Wijngaarden et al., 2009), hypogonadism and low levels of sex hormones (Kido et al., 2013; Vestergaard et al., 2004), low neuromuscular activity and marked hypotonia (Butler et al., 2001), or deficient intake of calcium and vitamin D (Lindmark et al., 2010) is unknown.

U.S. Pat. No. 8,198,327, herewith incorporated by reference in its entirety as if fully disclosed herein, discloses fatty acid amides of amino acids, e.g., oleoyl α-methyl serine and 2-methyl-oleoyl serine, and their use to stimulate bone growth, bone mass, or bone repair, or for prevention of bone loss.

SUMMARY OF INVENTION

In one aspect, the present invention relates to a method for improving bone mineral density or treating osteoporosis in a subject in need thereof, e.g., a subject suffering from Prader-Willi syndrome (PWS), said method comprising administering to said subject a therapeutically effective amount of a fatty acid amide of an amino acid, or a stereoisomer or salt thereof, wherein:
the fatty acid moiety is a moiety of a saturated fatty acid, mono-unsaturated fatty acid, or poly-unsaturated fatty acid, optionally substituted on at least one of its α- or β-positions by at least one group each independently is $(C_1\text{-}C_6)$alkyl, $-OR_1$, or $-SR_2$;
the amino acid moiety is a moiety of an amino acid optionally substituted at its α-position by at least one group each independently is $(C_1\text{-}C_6)$alkyl, or $-OR_3$; and
$R_1$, $R_2$, and $R_3$ each independently is H or $(C_1\text{-}C_6)$alkyl, provided that at least one of the fatty acid moiety and the amino acid moiety is substituted.

In particular embodiments, the fatty acid amide of an amino acid administered according to the method of the present invention is a compound of the formula I:

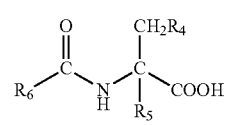

or a stereoisomer or salt thereof,
wherein: $R_4$ is $-OH$, $-SH$, phenyl, or hydroxyphenyl; $R_5$ is H, $(C_1\text{-}C_6)$alkyl, or $-OR_3$; $R_6$ is a group of the formula II:

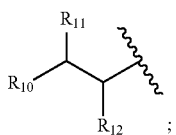

$R_{10}$ is $(C_{11}-C_{21})$alkyl, $(C_{11}-C_{21})$alkenyl, or $(C_{11}-C_{21})$alkynyl; and $R_{11}$ and $R_{12}$ each independently is H, $(C_1-C_6)$alkyl, —$OR_1$, or —$SR_2$, provided that at least one of $R_5$, $R_{11}$ and $R_{12}$ is not H. A more particular such compound is oleoyl α-methyl-serine (herein identified as HU-671), i.e., a compound of the formula I, wherein $R_4$ is —OH, $R_5$ is methyl, $R_{10}$ is —$(CH_2)_5CH$=$CH$—$(CH_2)_7$—$CH_3$, $R_{11}$ is H, and $R_{12}$ is H, or a stereoisomer or salt thereof.

In another aspect, the present invention provides a pharmaceutical composition for improving bone mineral density or treating osteoporosis in a subject in need thereof, e.g., a subject suffering from PWS, said composition comprising a fatty acid amide of an amino acid as defined above, e.g., a compound of the formula I as defined above, including HU-671, or a stereoisomer or salt thereof, and a pharmaceutically acceptable carrier.

In a further aspect, the present invention relates to a fatty acid amide of an amino acid as defined above, e.g., a compound of the formula I as defined above, including HU-671, or a stereoisomer or salt thereof, for use in improving bone mineral density or treating osteoporosis, e.g., in a subject suffering from PWS.

DETAILED DESCRIPTION

Figure 1A:
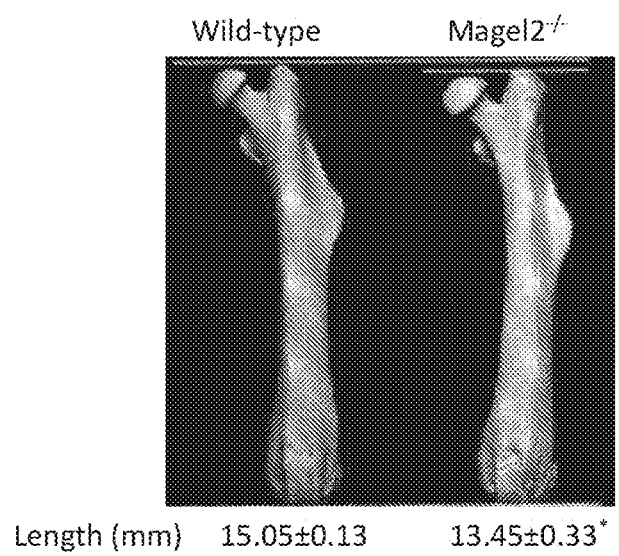
FIGS. 1A-1F show that in comparison with wild-type (WT) controls, 12-weeks old female Magel2-null mice show reduced femoral length (1A), BV/TV (1B), Tb.N (1C) and Conn.D (1D), as well as increased trabecular spacing (1E), and reduced Cort.Th (1F). Data are mean±SEM from 7-8 animals per group, *P<0.05 vs. wild-type littermate controls.
Figure 1B:
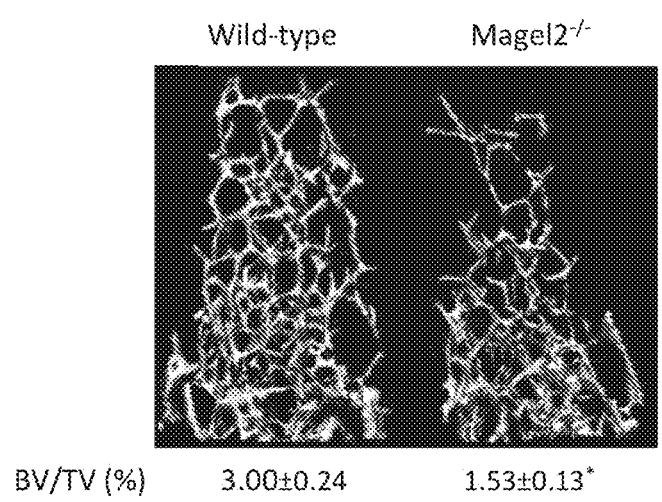
Figure 1C:
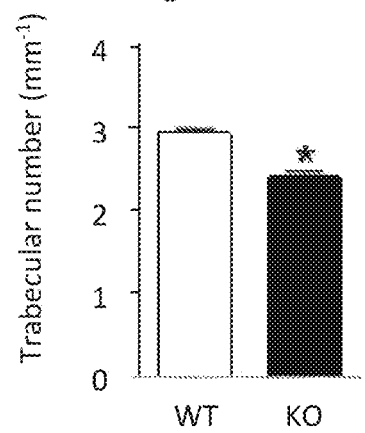
Figure 1D:
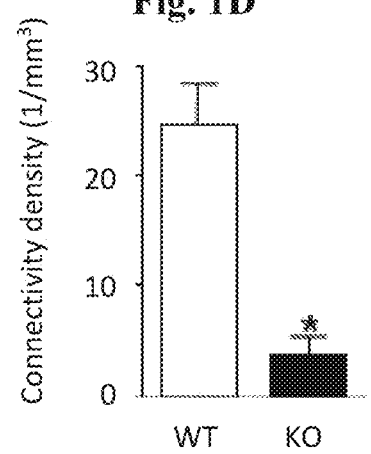
Figure 1E:
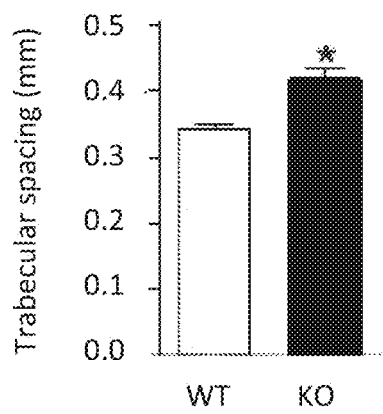
Figure 1F:
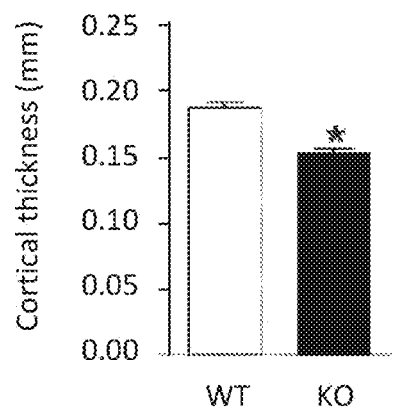

It has been found, in accordance with the present invention, that fatty acid amides of amino acids as disclosed in U.S. Pat. No. 8,198,327 are highly effective in improving bone mineral density or treating osteoporosis in a mouse model of PWS, as they are capable of inhibiting bone resorption thus slowing the rate of bone loss, and/or promoting bone deposition thus increasing bone density or bone thickness, wherein increase in bone mass and bone strength decreases the likelihood of bone fracture.

As particularly shown in the Experimental section herein, HU-671 completely prevented the trabecular bone loss observed in vehicle-treated Magel2-null mice, and stimulated increase in bone volume density (BV/TV), mainly by increasing Tb.N and enhancing the Tb.Th. Importantly, the rescue of PWS-induced bone loss by HU-671 was not selective only for the trabecular bone compartment, as evidenced by the fact that the cortical parameters were also improved. Chronic treatment with HU-671 was able to completely prevent the reduction in Cort.Th.

In one aspect, the present invention thus relates to a method for improving bone mineral density or treating osteoporosis in a subject in need thereof, e.g., a subject suffering from PWS, by administering to said subject a therapeutically effective amount of a fatty acid amide of an amino acid, or a stereoisomer or salt thereof, wherein (i) the fatty acid moiety is a moiety of a saturated fatty acid, mono-unsaturated fatty acid, or poly-unsaturated fatty acid, optionally substituted on at least one of its α- or β-positions by at least one group each independently is $(C_1-C_6)$alkyl, —$OR_1$, or —$SR_2$; (ii) the amino acid moiety is a moiety of an amino acid optionally substituted at its α-position by at least one group each independently is $(C_1-C_6)$alkyl, or —$OR_3$; and (iii) $R_1$, $R_2$, and $R_3$ each independently is H or $(C_1-C_6)$alkyl, provided that at least one of the fatty acid moiety and the amino acid moiety is substituted.

The term "subject" as used herein refers to any mammal such as a human, ape, cow, horse, dog, cat, whale, dolphin, and bat, but is preferably a human (individual).

The term "fatty acid amide of an amino acid" or "fatty acid amide", used herein interchangeably, refers to an amide formed upon conjugation of a fatty acid moiety and an amino acid moiety through the formation of an amide bond. It should be understood that while the fatty acid amide of an amino acid is generally referred to as a conjugate of a fatty acid moiety and an amino acid moiety, such a conjugate may be formed from a variety of precursors, employing a single or multi-step synthetic methodologies.

The term "fatty acid moiety" as used herein refers to an acyl moiety derivable from a fatty acid, i.e., being generally of the form RC(=O)—, wherein R represents the aliphatic chain of the corresponding fatty acid, and wherein the point of attachment of the fatty acid moiety to the amino acid moiety of the fatty acid amide is through the carbonyl carbon atom of the fatty acid moiety.

The term "fatty acid" as used herein denotes a mono carboxylic acid having an aliphatic chain ("tail"), wherein said aliphatic chain may be saturated, mono-unsaturated (having one unsaturated bond anywhere on the aliphatic chain), or poly unsaturated (having at least two unsaturated bonds anywhere on the aliphatic chain). An unsaturated bond on the aliphatic chain may be a double (in the cis and/or trans configuration) or a triple bond. The length of the aliphatic chain (being saturated, monounsaturated or polyunsaturated) of a fatty acid may vary between 7-23 carbon atoms. Fatty acids may be derived from a natural source (either an animal or plant source), synthetic source or semi-synthetic source.

Examples of saturated fatty acids include, without being limited to, lauric acid, myristic acid, palmitic acid and stearic acid. Non-limiting examples of monounsaturated fatty acids are myristoleic acid, palmitoleic acid, oleic acid, elaidic acid and vaccenic acid. Examples of polyunsaturated fatty acids include, without limiting, linoleic acid, α-linolenic acid, γ-linolenic acid, arachidonic acid, eicosapentaenoic acid, erucic acid and docosahexaenoic acid.

In certain embodiments, the fatty acid moiety constituting the fatty acid amide as defined herein is a moiety of a saturated fatty acid. In other embodiments, said fatty acid moiety is a moiety of a mono-unsaturated fatty acid. In further embodiments, said fatty acid moiety is a moiety of a poly-unsaturated fatty acid.

In particular embodiments, said fatty acid moiety is a moiety of a mono- or poly-unsaturated fatty acid of the formula R—COOH, wherein R represents an aliphatic chain consisting of 13-23, e.g., 17, carbon atoms and having one or more double bonds (each in the cis or trans configuration). In more particular such embodiments, the fatty acid moiety is an oleoyl fatty acid moiety of the formula $CH_3(CH_2)_7CH=CH(CH_2)_7C(O)—$, derived from the corresponding oleic acid.

According to the present invention, the saturated-, mono-unsaturated-, or poly-unsaturated-fatty acid from which the fatty acid moiety is derived may optionally be substituted on at least one of its α- or β-positions by at least one group each independently selected from $(C_1-C_6)$alkyl, $\beta OR_1$, or —$SR_2$, wherein $R_1$ and $R_2$ each independently is H or $(C_1-C_6)$alkyl. In certain embodiments, the fatty acid moiety is unsubstituted. In other embodiments, the fatty acid moiety is substituted at its α-position, at its β-position, or at both of its α- and β-positions.

As known in the art, the phrase "α-position of the fatty acid moiety" refers to the carbon atom on the aliphatic chain of the fatty acid moiety that is directly adjacent to the carbonyl carbon atom of the fatty acid moiety; and the phrase "β-position of the fatty acid moiety" refers to the carbon atom on the aliphatic chain of the fatty acid moiety that is the second carbon atom adjacent to the carbonyl carbon atom of the fatty acid moiety.

In particular embodiments, the fatty acid moiety is substituted on at least one of its α- or β-positions by at least one group each independently selected from $(C_1-C_6)$alkyl, more particularly methyl, ethyl, or isopropyl.

The term "amino acid moiety" as used herein refers to a group derivable from an amino acid, i.e., an organic compound comprising both amine and carboxylic acid functional groups, upon removal of a hydrogen atom from an amino group thereof, wherein the point of attachment of the amino acid moiety to the fatty acid moiety of the fatty acid amide is through the amine of said amino group.

The amino acid may be either natural (i.e., being generally of the formula $H_2N—CHR—COOH$ wherein R is an organic substituent) or non-natural (i.e., derived from synthetic or semi-synthetic source) amino acid. The twenty two natural amino acids are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of non-natural amino acids include diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, p-propargyl-oxy-phenylalanine, m-ethynyl-phenylalanine, p-bromophenylalanine, p-iodophenylalanine, p-azidophenylalanine, p-acetylphenylalanine, azidonorleucine, 6-ethynyl-tryptophan, 5-ethynyl-tryptophan, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine. An amino acid as used herein may be in either the L- or D-configuration, or a mixture consisting of both L- and D-configurations.

In certain embodiments, the amino acid moiety constituting the fatty acid amide as defined herein is a moiety of a natural amino acid, e.g., serine, cysteine, tyrosine, or phenylalanine, but particularly serine.

According to the present invention, the amino acid from which the amino acid moiety is derived may optionally be substituted at its α-position by at least one group each independently selected from $(C_1-C_6)$alkyl, or —$OR_3$, wherein $R_3$ is H or $(C_1-C_6)$alkyl. In certain embodiments, said amino acid is substituted at its α-position by $(C_1-C_6)$alkyl, e.g., methyl, ethyl, or isopropyl.

In certain embodiments, the fatty acid amide administered according to the method of the present invention is a compound of the formula I:

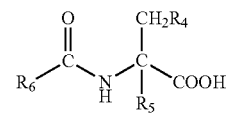

or a stereoisomer or salt thereof,
wherein:
$R_4$ is —OH, —SH, phenyl, or hydroxyphenyl;
$R_5$ is H, $(C_1-C_6)$alkyl, or —$R_3$;
$R_6$ is a group of the formula II:

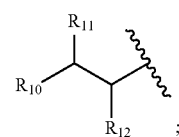

$R_{10}$ is $(C_{11}-C_{21})$alkyl, $(C_1-C_{21})$alkenyl, or $(C_{11}-C_{21})$alkynyl; and
$R_{11}$ and $R_{12}$ each independently is H, $(C_1-C_6)$alkyl, —$OR_1$, or —$SR_2$,
provided that at least one of $R_5$, $R_{11}$ and $R_{12}$ is not H.

The term "alkyl" typically means a monovalent linear (unbranched) or branched hydrocarbon radical. When referring to "$(C_1-C_6)$alkyl" it should be understood to encompass any linear or branched alkyl having 1, 2, 3, 4, 5, or 6 carbon atoms, such as methyl, ethyl, n-propyl, isopropyl, n-butyl, sec-butyl, isobutyl, tert-butyl, n-pentyl, 2-pentyl, 3-pentyl, 2-methylbutyl, 2,2-dimethylpropyl, n-hexyl, 2-hexyl, 3-hexyl, 2-propyl, and the like. Similarly, when referring to "$(C_{11}-C_{21})$alkyl" it should be understood to encompass any linear or branched alkyl having 11, 12, 13, 14, 15, 16, 17, 18, 19, 20, or 21 carbon atoms.

The term "alkenyl" typically means a monovalent linear (unbranched) or branched hydrocarbon radical having at least one double bond, which may be between any two carbon atoms of the alkenyl chain and either in the cis or trans (or the E or Z) configuration. When referring to "$(C_{11}-C_{21})$alkenyl" it should be understood to encompass any linear or branched alkenyl having 11, 12, 13, 14, 15, 16, 17, 18, 19, 20, or 21 carbon atoms.

The term "alkynyl" typically means a monovalent linear (unbranched) or branched hydrocarbon radical having at least one triple bond, which may be between any two carbon atoms of the alkynyl chain. When referring to "$(C_{11}-C_{21})$alkynyl" it should be understood to encompass any linear or branched alkynyl having 11, 12, 13, 14, 15, 16, 17, 18, 19, 20, or 21 carbon atoms.

The term "phenyl" means a —$C_6H_5$ ring radical; and the term "hydroxyphenyl" refers to a phenyl ring substituted with a hydroxyl group on any one of ortho-, meta-, or para-positions of the ring relative to the point of attachment to the phenyl ring.

In certain embodiments, the amino acid conjugated to the fatty acid in the compound of the formula I is serine, cysteine, phenylalanine, or tyrosine, i.e., a compound of the formula I, wherein $R_4$ is —OH, —SH, phenyl, or 4-hydroxyphenyl, respectively. In particular such embodiments, said amino acid is serine, i.e., $R_4$ is —OH.

In certain embodiments, the amino acid conjugated to the fatty acid in the compound of the formula I is unsubstituted, wherein $R_5$ is H. In other embodiments, said amino acid is substituted, wherein $R_5$ is $(C_1-C_6)$alkyl, —OH, or —O—$(C_1-C_6)$alkyl, e.g., wherein $R_5$ is $(C_1-C_6)$alkyl such as methyl, ethyl or isopropyl.

In certain embodiments, the fatty acid conjugated to the amino acid in the compound of the formula I is a mono- or poly-unsaturated fatty acid of the formula R—COOH, wherein R represents an aliphatic chain consisting of 13-23 carbon atoms and having 1, 2, 3, 4, 5, or 6 double bonds (each in the cis or trans configuration), i.e., wherein $R_{10}$ is $(C_{11}-C_{21})$alkenyl. In particular such embodiments, said fatty acid has an aliphatic chain consisting of 17 carbon atom (i.e., $R_{10}$ is $C_{15}$-alkenyl) and having one or more double bonds, such as oleic acid, elaidic acid, vaccenic acid, linoleic acid, α-linolenic acid, γ-linolenic acid, and stearidonic acid. More particular such embodiments are those wherein said fatty acid is oleic acid optionally substituted on at least one of its α- or β-positions i.e., wherein $R_{10}$ is —$(CH_2)_5$—CH=CH—$(CH_2)_7$—$CH_3$.

In certain embodiments, the fatty acid conjugated to the amino acid in the compound of the formula I is unsubstituted, i.e., $R_{10}$ and α- or β-positions, i.e., at least one of $R_{11}$ and $R_{12}$ each independently is $(C_1-C_6)$alkyl such as methyl, ethyl or isopropyl, —$OR_1$, or —$SR_2$, wherein $R_1$ and $R_2$ each independently is H or $(C_1-C_6)$alkyl such as methyl, ethyl or isopropyl.

In certain embodiments, the fatty acid amide used according to the present invention is a compound of the formula I, wherein $R_4$ is —OH; $R_5$ is H or $(C_1-C_6)$alkyl; $R_{10}$ is $(C_{11}-C_{21})$alkenyl; and $R_{11}$ and $R_{12}$ each independently is H or $(C_1-C_6)$alkyl. Particular such compounds are those wherein $R_5$ is H, methyl, ethyl, or isopropyl; $R_{11}$ is $(C_{15})$alkenyl; and $R_{11}$ and $R_{12}$ each independently is H, methyl, ethyl or isopropyl. More particular such embodiments are those wherein $R_{10}$ is —$(CH_2)_5$—CH=CH—$(CH_2)_7$—$CH_3$.

In specific embodiments, the fatty acid amide used according to the present invention is a compound of the formula I, wherein $R_4$ is —OH; $R_{10}$ is —$(CH_2)_5$—CH=CH—$(CH_2)_7$—$CH_3$; and: (i) $R_5$ is methyl, $R_{11}$ is H, and $R_{12}$ is H (oleoyl α-methyl-serine, HU-671; formula III in Table 1); (ii) $R_5$ is methyl, $R_{11}$ is H, and $R_{12}$ is methyl; (iii) $R_5$ is methyl, $R_{11}$ is methyl, and $R_{12}$ is H (formula IV in Table 1); (iv) $R_5$ is methyl, $R_{11}$ is methyl, and $R_{12}$ is methyl; (v) $R_5$ is H, $R_{11}$ is H, and $R_{12}$ is methyl (2-methyl-oleoyl serine; formula V in Table 1); (vi) $R_5$ is H, $R_{11}$ is methyl, and $R_{12}$ is H; or (vii) $R_5$ is H, $R_{11}$ is methyl, and $R_{12}$ is methyl. In such a particular embodiment, the fatty acid amide used according to the present invention is HU-671, or a stereoisomer or salt thereof.

TABLE 1

Specific fatty acid amides disclosed herein

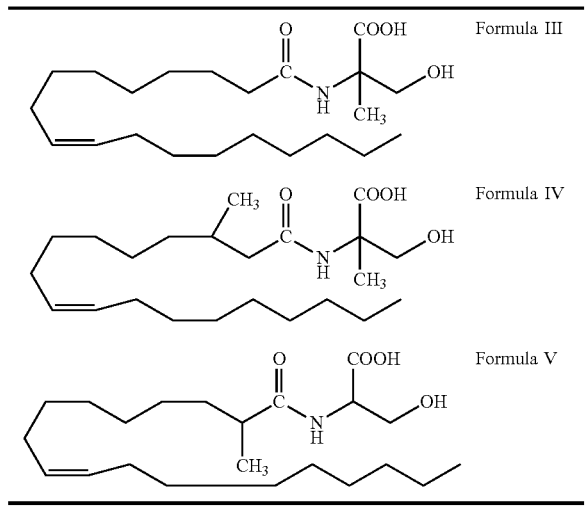

The active agent administered according to the method of the present invention is a fatty acid amide as defined in any one of the embodiments above, a stereoisomer thereof, or a pharmaceutically acceptable salt thereof.

The term "stereoisomer" as used herein means an isomer that possess identical constitution as a corresponding stereoisomer, but which differs in the arrangement of its atoms in space from the corresponding stereoisomer. For example, stereoisomers may be enantiomers (optical isomers, i.e., R, S, or racemate, wherein a certain enantiomer may have an optical purity of 90%, 95%, 99% or more), diastereomers and/or cis-trans (E/Z) isomers. It should be understood that a composition including a fatty acid amide may include enantiomers, single diastereomers, as well as mixtures thereof at any ratio (e.g., racemic mixtures, non-racemic mixtures, mixtures of at least two diastereisomers, and so forth). Furthermore, the present disclosure encompasses any stereoisomer of a fatty acid amide achieved through in vivo or in vitro metabolism, or by any type of synthetic route.

Optically active forms of the fatty acid amides used according to the present invention may be prepared using any method known in the art, e.g., by resolution of the racemic form by recrystallization techniques; by chiral synthesis; by extraction with chiral solvents; or by chromatographic separation using a chiral stationary phase. A non-limiting example of a method for obtaining optically active materials is transport across chiral membranes, i.e., a technique whereby a racemate is placed in contact with a thin membrane barrier, the concentration or pressure differential causes preferential transport across the membrane barrier, and separation occurs as a result of the non-racemic chiral nature of the membrane that allows only one enantiomer of the racemate to pass through. Chiral chromatography, including simulated moving bed chromatography, can also be used. A wide variety of chiral stationary phases are commercially available.

The term "salt" as used herein refers to any salt obtained by acid or base addition. In some embodiments, the salt is an acid addition salt obtained by protonation of a fatty acid amide, e.g., at the amidic moiety. Suitable pharmaceutically acceptable acid addition salts include, without being limited to, the mesylate salt, the maleate salt, the fumarate salt, the tartrate salt, the hydrochloride salt, the hydrobromide salt, the esylate salt, the p-toluenesulfonate salt, the benzenesulfonate salt, the benzoate salt, the acetate salt, the phosphate salt, the sulfate salt, the citrate salt, the carbonate salt, and the succinate salt. In other embodiments, the salt is a base addition salt obtained by deprotonation of a proton from the fatty acid amide, e.g., from the acidic moiety (—COOH) of the fatty acid amide. Counter ions forming a salt of a fatty acid amide can, in a non-limiting fashion, include one or more inorganic or organic cations, which in some embodiments are pharmaceutically acceptable, such as alkaline metal cations, e.g., lithium, sodium or potassium cation; alkaline earth metal cations, e.g., calcium or magnesium cation; and ammonium ($NH_4^+$) or an organic cation derived from an amine of the formula $(R)_4N^+$, wherein each one of the Rs independently is selected from H, $C_1$-$C_{22}$, preferably $C_1$-$C_6$ alkyl, such as methyl, ethyl, propyl, isopropyl, n-butyl, sec-butyl, isobutyl, tert-butyl, n-pentyl, 2,2-dimethylpropyl, n-hexyl, and the like, phenyl, or heteroaryl such as pyridyl, imidazolyl, pyrimidinyl, and the like, or two of the Rs together with the nitrogen atom to which they are attached form a 3-7 membered ring optionally containing a further heteroatom selected from N, S and O, such as pyrrolydine, piperidine and morpholine.

The fatty acid amides used according to the present invention may be synthesized according to any technology or procedure known in the art, e.g., as described in detail in U.S. Pat. No. 8,198,327 and exemplified herein with respect to HU-671.

Pharmaceutically acceptable salts of the fatty acid amide may be formed by conventional means, e.g., by reacting a free base form of the active agent with one or more equivalents of the appropriate acid in a solvent or medium in which the salt is insoluble, or in a solvent such as water which is removed in vacuo or by freeze drying, or by exchanging the anion/cation of an existing salt for another anion/cation on a suitable ion exchange resin.

In certain embodiments, the method of the present invention according to any one of the embodiments defined above comprises administering said fatty acid amide in combination with an additional active agent, wherein the administration of said fatty acid amide and said additional active agent is carried out either concomitantly or sequentially at any order.

Non-limiting examples of active agents that might be administered according to the method of the invention, in addition to the fatty acid amide, include a bisphosphonate such as alendronate, risedronate, ibandronate, or zoledronic acid; a hormone such as calcitonin, estrogens, testosterone, thyroid hormone, parathyroid hormone, or growth hormone; an anti-receptor activator of nuclear factor kappa-B ligand (anti-RANKL) such as denosumab; a cathepsin K inhibitor such as odanacatib; or an anti-sclerostin antibody such as romosozumab.

Suitable amounts of any additional active agent can be determined by routine experimentation considering all the usual dosing factors including the amount of fatty acid amid to be administered, the dosing regimen, and the condition to be treated (e.g., PWS). The compositions can be administered in single or divided doses, preferably with the total daily dose divided into equal dosages taken over the course of a day. Preferably, only one or two doses per day will be required. In one embodiment, the composition that is administered will be taken with food and drink (e.g., within about 2 hours of eating, preferably within about one hour of eating) so as to eliminate any potential gastrointestinal distress. In another embodiment, the compositions may be administered without regard to eating, while in a further embodiment, the active agent(s) can be included in a food product and administered as a food product. The active agents, when more than one is included, may be administered concurrently or sequentially, and in the latter event, at different times.

In another aspect, the present invention provides a pharmaceutical composition for improving bone mineral density or treating osteoporosis in a subject in need thereof, e.g., a subject suffering from PWS, said composition comprising, as an active agent, a fatty acid amide of an amino acid as defined in any one of the embodiments above, or a stereoisomer or salt thereof, and a pharmaceutically acceptable carrier.

In certain embodiments, the fatty acid amide comprised within the pharmaceutical composition of the invention is a compound of the formula I as defined in any one of the embodiments above, or a stereoisomer or salt thereof. Particular such compounds are those formed upon conjugation of oleic acid optionally substituted on at least one of its α- or β-positions with a group independently selected from ($C_1$-$C_6$)alkyl, —OH, —O—($C_1$-$C_6$)alkyl, —SH, or —S—($C_1$-$C_6$)alkyl, and serine optionally substituted at its α-position with ($C_1$-$C_6$)alkyl, —OH, or —O—($C_1$-$C_6$)alkyl, i.e., a compound of the formula I, wherein $R_4$ is —OH, and $R_{10}$ is $(CH_2)_5$—CH=CH—$(CH_2)_7$—$CH_3$, or stereoisomers or salts thereof. More particular such compounds are those wherein (i) $R_5$ is methyl, $R_{11}$ is H, and $R_{12}$ is H (HU-671); (ii) $R_5$ is methyl, $R_{11}$ is H, and $R_{12}$ is methyl; (iii) $R_5$ is methyl, $R_{11}$ is methyl, and $R_{12}$ is H; (iv) $R_5$ is methyl, $R_{11}$ is methyl, and $R_{12}$ is methyl; (v) $R_5$ is H, $R_{11}$ is H, and $R_{12}$ is methyl; (vi) $R_5$ is H, $R_{11}$ is methyl, and $R_{12}$ is H; or (vii) $R_5$ is H, $R_{11}$ is methyl, and $R_{11}$ is methyl, or stereoisomers or salts thereof. In a specific embodiment, the fatty acid amide comprised within the pharmaceutical composition of the invention is the compound herein identified HU-671, or a stereoisomer or salt thereof.

The pharmaceutical composition of the present invention may be administered in combination with an additional active agent such as a bisphosphonate, hormone, anti-RANKL, cathepsin K inhibitor, or anti-sclerostin antibody, wherein said fatty acid amide and said additional active agent are administered either concomitantly (when composing either a sole composition or two separate compositions), or sequentially at any order.

The pharmaceutical compositions provided by the present invention may be prepared by conventional techniques, e.g., as described in Remington: The Science and Practice of Pharmacy, 19$^{th}$ Ed., 1995. The compositions can be prepared by any method well known in the art of pharmacy, e.g., by uniformly and intimately bringing an active agent as defined above or a combination thereof into association with an auxiliary agent(s) (also referred to as a pharmaceutically acceptable carrier), e.g., a liquid carrier, a finely divided solid carrier, or both, and then, if necessary, shaping the product into the desired formulation. The compositions may be in liquid, solid or semisolid form, wherein the auxiliary agent(s) is typically selected from those conventional in the art, such as carriers, fillers, binders, diluents, disintegrants, adjuvants, lubricants, colorants, flavoring agents, anti-oxidants, and wetting agents. In one embodiment, the pharmaceutical composition of the present invention is formulated as nanoparticles.

The compositions can be formulated for any suitable route of administration, i.e., for oral administration; parenteral, e.g., intravenous, intraarterial, intramuscular, intradermal, intraperitoneal, intrathecal, intrapleural, intratracheal, subcutaneous, rectal, nasal, vaginal or topical, administration; or inhalation. The dosage will depend on the state of the subject treated; will vary according to the age, body weight, and response of said subject; and will be determined as deemed appropriate by the practitioner.

In certain embodiments, the daily dosage of the fatty acid amide is based on the body weight of the subject to be treated. For example, a patient can be dosed from about 0.1 mg/kg to about 5.0 mg/kg a day, including about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, and about 4.5 mg/kg, a day.

The pharmaceutical compositions of the invention may be administered, e.g., continuously, daily, twice daily, thrice daily or four times daily, for various duration periods, e.g., days, weeks, months, years, or decades.

Pharmaceutical compositions suitable for oral administration may be presented as discrete dosage units, such as pills, tablets, dragees or capsules, or as a powder or granules, or as a solution or suspension. The active agent may also be presented as a bolus or paste. The compositions may further be processed into a suppository or enema for rectal administration.

In various embodiments, the pharmaceutical composition is a solid oral dosage form. Solid oral dosage forms typically include a variety of auxiliary agents including one or more diluents, lubricants, disintegrants, binders, fillers, dyes, and antioxidants.

Suitable diluents for use in the solid oral dosage form include, e.g., pharmaceutically acceptable inert fillers such as microcrystalline cellulose such as that sold under the Trademark Avicel® (FMC Corp., Philadelphia, Pa.), e.g., Avicel®pH101, Avicel®pH102 and Avicel®pH112; lactose such as lactose monohydrate, lactose anhydrous, and Pharmatose DCL21; dibasic calcium phosphate such as Emcompress®; saccharides such as sucrose and glucose; starch; sugar alcohols such as mannitol and sorbitol; and/or combinations of any of the foregoing.

Suitable lubricants, including agents that act on the flowability of the powder to be compressed are, e.g., colloidal silicon dioxide such as Aerosil®200; talc; hydrogenated vegetable oils; stearic acid, magnesium stearate, and calcium stearate; and combinations thereof. The amount of lubricant may vary within a range of from 0.1 to 5.0% by weight of the pharmaceutical composition.

Suitable disintegrants include, e.g., lightly crosslinked polyvinyl pyrrolidone, cross-povidone, sodium starch glycolate, crosslinked sodium carboxymethylstarch, and combinations, and combinations thereof. The amount of disintegrant may vary within a range of from about 2 to about 20% by weight, e.g., about 15% by weight of the pharmaceutical composition.

Binders are added to pharmaceutical compositions to help hold such compositions together and release the medicament therefrom. Suitable binders include povidones, starches, celluloses (microcrystalline cellulose), alginates, gums, hydroxypropyl methylcellulose (HPMC), hydroxypropylcellulose (HPC), carboxymethylcellulose sodium, polyvinyl pyrrolidone (PVP), or sugars, starches or other pharmaceutically acceptable substances with cohesive properties, or combinations thereof. The amount of binder may vary within a range of from about 10 to about 45% by weight, e.g., about 20 to about 30% by weight of the pharmaceutical composition.

Examples of dyes include iron oxides, titanium dioxide, triphenylmethane dyes, azo dyes, quinoline dyes, indigotine dyes, carotenoids, for coloring the dosage forms, and opacifying agents such as titanium dioxide or talc in order to reduce the transparency to light and to save on dyes, and combinations thereof.

Representative antioxidants include ascorbic acid; alpha tocopherol; ascorbyl palmitate; ascorbates; isoascorbates; butylated hydroxyanisole; butylated hydroxytoluene; nordihydroguiaretic acid; esters of gallic acid comprising at least 3 carbon atoms comprising a member selected from the group consisting of propyl gallate, octyl gallate, decyl gallate, decyl gallate; 6-ethoxy-2,2,4-trimethyl-1,2-dihydroguinoline; N-acetyl-2,6-di-t-butyl-p-aminophenol; butyl tyrosine; 3-tertiarybutyl-4-hydroxyanisole; 2-tertiary-butyl-4-hydroxyanisole; 4-chloro-2,6-ditertiary butyl phenol; 2,6-ditertiary butyl p-methoxy phenol; 2,6-ditertiary butyl-p-cresol:polymeric antioxidants; trihydroxybutyro-phenone physiologically acceptable salts of ascorbic acid, erythorbic acid, and ascorbyl acetate; calcium ascorbate; sodium ascorbate; sodium bisulfite; and the like; and any combination thereof. The amount of antioxidant used is about 0.001% to about 25% by weight of the pharmaceutical composition.

In some embodiments, the pharmaceutical composition is an oral liquid dosage form. Oral liquid dosage forms typically include one or more solvents, suspending agents, dispersing agents, sweetening agents, preservatives, buffering agents, antioxidants, chelating agents, surfactants, flavoring agents, coloring agents, and viscosity-modifying agents.

Suitable solvents may be selected from water, purified water, ethanol, isopropyl alcohol, glycerin, propylene glycol, mineral oil, and mixtures thereof.

Representative dispersing agents may be selected from magnesium aluminum silicate, xanthan gum, cellulose compounds, acacia, tragacanth, kaolin, pectin, or mixtures thereof.

One or more sweetening agents may be selected from sucrose, saccharin sodium, aspartame, sucralose, and mixtures thereof. The sweetening agents may be provided in an amount equal to between about 0.05 to about 50% by weight of the pharmaceutical composition. Suitable sugars illustratively include glucose, fructose, xylitol, tagatose, maltitol, isomaltulose, Isomalt™ (hydrogenated isomaltulose), lactitol, sorbitol, mannitol, trehalose, maltodextrin, polydextrose, etc., or a combination thereof. Other sweeteners illustratively include glycerin, erythritol, maltol, acesulfame and salts thereof, e.g., acesulfame potassium, alitame, aspartame, neotame, cyclamate, saccharin and salts thereof, e.g., saccharin sodium, neohesperidin dihydrochalcone, stevioside, thaumatin, etc., or a combination thereof.

Suitable preservatives may be selected from methylparaben, propylparaben, butylparaben, sorbic and benzoic acids and salts thereof, or a combination thereof, particularly the sodium and potassium salts, phenol, alkyl esters of parahydroxybenzoic acid, sorbic acid, o-phenylphenol benzoic acid and the salts thereof, chlorobutanol, benzyl alcohol, thimerosal, phenylmercuric acetate and nitrate, nitromersol, benzalkonium chloride, and cetylpyridinium chloride and mixtures thereof. The preservatives may be provided in an amount equal to between about 0.05 to about 5% by weight of the pharmaceutical composition.

Suitable buffer systems include, but are not limited to, NaOH, acetic, boric, carbonic, phosphoric, succinic, malaic, tartaric, citric, benzoic, lactic, glyceric, gluconic, glutaric and glutamic acids and their sodium, potassium and ammonium salts, and any combination thereof. The pharmaceutical compositions generally contain from about 0.1% to about 20% buffer systems by weight of the pharmaceutical composition.

The oral liquid dosage form may contain an antioxidant to slow or effectively stop the rate of any autoxidizable material present in the dosage form. Representative antioxidants include a member selected from ascorbic acid; alpha tocopherol; ascorbyl palmitate; ascorbates; isoascorbates; butylated hydroxyanisole; butylated hydroxytoluene; nordihydroguiaretic acid; esters of gallic acid comprising at least 3 carbon atoms comprising a member selected from the group consisting of propyl gallate, octyl gallate, decyl gallate, decyl gallate; 6-ethoxy-2,2,4-trimethyl-1,2-dihydro-guinoline; N-acetyl-2,6-di-t-butyl-p-aminophenol; butyl tyrosine; 3-tertiarybutyl-4-hydroxyanisole; 2-tertiary-butyl-4-hydroxyanisole; 4-chloro-2,6-ditertiary butyl phenol; 2,6-ditertiary butyl p-methoxy phenol; 2,6-ditertiary butyl-p-cresol; polymeric antioxidants; trihydroxybutyro-phenone physiologically acceptable salts of ascorbic acid, erythorbic acid, and ascorbyl acetate; calcium ascorbate; sodium ascorbate; sodium bisulfite; and the like; and any combination thereof. The amount of antioxidant used is about 0.001% to about 25% by weight of the pharmaceutical composition.

The dosage form may also contain a chelating agent to protect the active agent either during storage or when in use. Examples of chelating agents include, e.g., polyacrylic acid, citric acid, edetic acid, disodium edetic acid, and the like; and combinations thereof.

The oral liquid dosage form may also comprise a surfactant or a mixture of surfactants where the surfactant is selected from nonionic, anionic and cationic surfactants. Exemplary nontoxic, nonionic surfactants suitable for forming a composition comprise alkylated aryl polyether alcohols known as Triton®; polyethylene glycol tertdodecyl throether available as Nonic®; fatty and amide condensate or Alrosol®; aromatic polyglycol ether condensate or Neutronyx®; fatty acid alkanolamine or Ninol®; sorbitan monolaurate or Span®; polyoxyethylene sorbitan esters or Tweens®; sorbitan monolaurate polyoxyethylene or Tween 20®; sorbitan mono-oleate polyoxyethylene or Tween 80®; polyoxypropylene-polyoxyethylene or Pluronic®; polyglycolyzed glycerides such as Labrasol®; polyoxyethylated castor oil such as Cremophor® and polyoxypropylene-polyoxyethylene-8500 or Pluronic®; or any combination thereof. By way of example, anionic surfactants may comprise sulfonic acids and the salts of sulfonated esters such as sodium lauryl sulfate, sodium sulfoethyl oleate, dioctyl sodium sulfosuccinate, cetyl sulfate sodium, myristyl sulfate sodium; sulfated esters; sulfated amides; sulfated alcohols; sulfated ethers; sulfated carboxylic acids; sulfonated aromatic hydrocarbons; sulfonated ethers; and the like, or any combination thereof. The cationic surface active agents comprise cetyl pyridinium chloride; cetyl trimethyl ammonium bromide; diethylmethyl cetyl ammonium chloride; benzalkonium chloride; benzethonium chloride; primary alkylammonium salts; secondary alkylammonium salts; tertiary alkylammonium salts; quaternary alkylammonium salts; acylated polyamines; salts of heterocyclic amines; palmitoyl carnitine chloride, behentriamonium methosulfate, and the like, or any combination thereof.

A flavoring agent or flavorant may be added to the liquid dosage or other oral dosage form. A "flavoring agent," as herein is a substance capable of enhancing taste or aroma of a composition. Suitable natural or synthetic flavoring agents can be selected from standard reference books, for example Fenaroli's Handbook of Flavor Ingredients, $3^{rd}$ edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, vanilla, wintergreen, etc., or any combination thereof. Also useful, particularly where the composition is intended primarily for pediatric use, is tutti-frutti or bubble-gum flavor, a compounded flavoring agent based on fruit flavors. Flavoring agents can be used singly or in combinations of two or more. Typically the flavoring agent, or an oil or essence including the flavoring agent, if present is at a concentration in the pharmaceutical composition of about 0.1 to about 5 mg/ml, preferably about 0.2 to about 3 mg/ml, and most preferably about 0.5 to about 2 mg/ml.

Optionally, the liquid (or other) dosage form further includes a coloring agent. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide, and mixtures thereof. Illustratively, FD&C Red #40 is present at a concentration in the composition of 0 to about 3 mg/ml, preferably 0 to about 2 mg/ml, and most preferably 0 to about 1 mg/ml.

Viscosity-modifying agents may be added to the liquid (or other) dosage form and include, but are not limited to, methylcellulose, sodium carboxymethylcellulose, hydroxypropyl-methylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions typically include about 0.1% to about 5% of viscosity-modifying agents by weight of the pharmaceutical composition.

The pharmaceutical composition of the invention may be in the form of a sterile injectable aqueous or oleagenous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution, polyethylene glycol (PEG), 2-hydroxypropyl-β-cyclodextrin (HPCD), Tween-80, and isotonic sodium chloride solution. The compositions may be presented in unit-dose or multi-dose containers, for example sealed vials and ampoules, and may be stored in a freeze-dried (lyophilized) condition requiring only the addition of sterile liquid carrier, e.g., water, prior to use. For transdermal administration, e.g., gels, patches or sprays can be contemplated. Compositions or formulations suitable for pulmonary administration, e.g., by nasal inhalation include fine dusts or mists which may be generated by means of metered dose pressurized aerosols, nebulizers or insufflators.

In a further aspect, the present invention relates to a fatty acid amide of an amino acid as defined in any one of the embodiments above, or a stereoisomer or salt thereof, for use in improving bone mineral density or treating osteoporosis, e.g., in a subject suffering from PWS.

In certain embodiments, the fatty acid amide used is a compound of the formula I as defined in any one of the embodiments above, e.g., such a compound wherein $R_4$ is —OH; $R_{10}$ is —(CH$_2$)$_5$—CH=CH—(CH$_2$)$_7$—CH$_3$; and (i) $R_5$ is methyl, $R_{11}$ is H, and $R_{12}$ is H (HU-671); (ii) $R_5$ is methyl, $R_{11}$ is H, and Ria is methyl; (iii) $R_5$ is methyl, $R_{11}$ is methyl, and $R_{12}$ is H; (iv) $R_5$ is methyl, $R_{11}$ is methyl, and $R_{12}$ is methyl; (v) $R_5$ is H, $R_{11}$ is H, and $R_{12}$ is methyl; (vi) $R_5$ is H, $R_{11}$ is methyl, and Ria is H; or (vii) $R_5$ is H, $R_{11}$ is methyl, and $R_{12}$ is methyl, or a stereoisomer or salt thereof.

The term "improve/improving bone mass density" as used herein means stimulating bone mass (e.g., increasing bone mass), decreasing bone resorption, and/or preventing bone loss. Administration of a fatty acid amide as disclosed herein, without being bound by theory, will lead to a substantial increase in bone formation, decreased bone resorption, and reversal of bone loss in patients with PWS. Thus, the fatty acid amide and optionally other active agent(s) disclosed herein may be used for the treatment (including prevention or alleviation) of a disease, disorder, or condition associated with bone loss or low bone density, or to inhibit osteoclast stimulation and/or bone resorption.

In various embodiments, the fatty acid amide administered according to the method disclosed herein improves one or more bone parameters such as bone volume density (BV/TV), trabecular number (Tb.N), and trabecular thickness (Tb.Th). The term "bone volume density" refers to the fraction of a given volume of bone (total volume or TV) that is comprised of calcified matter (bone volume or BV). Therefore, bone volume density is calculated as BV/TV and reported as a percentage.

Unless otherwise indicated, all numbers used in this specification are to be understood as being modified in all instances by the term "about". Accordingly, unless indicated to the contrary, the numerical parameters set forth in this specification are approximations that may vary by up to plus or minus 10% depending upon the desired properties to be obtained by the present invention.

The invention will now be illustrated by the following non-limiting Examples.

EXAMPLES

Example 1. Synthesis of N-oleoyl α-methyl-DL-serine (HU-671)

Preparation of N-hydroxysuccinimide Ester of Oleic Acid

Oleic acid (2 g, 7.08 mmoles) was added to a solution of N-hydroxysuccinimide (0.814 g, 7.08 mmoles) in dry ethyl acetate (30 ml). A solution of dicyclohexylcarbodiimide (1.45 g, 7.08 mmoles) in dry ethyl acetate (2.5 ml) was then added, and the reaction mixture was left overnight at room temperature. Dicyclohexylurea was filtered, and the crude material was chromatographed on silica gel (eluting with chloroform) to give 2.38 g (85%) as yellowish oil.

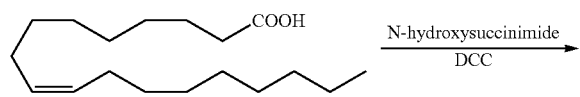

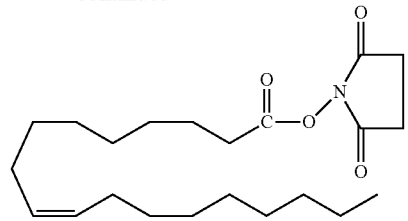

Preparation of N-oleoyl α-methyl-DL-serine

A solution of N-hydroxysuccinimide ester of oleic acid (395 mg, 1 mmole) in tetrahydrofuran (10 ml) was added to a solution of αmethyl-DL-serine (119.1 mg, 1 mmole) and sodium bicarbonate (84 mg, 1 mmole) in water (10 ml). The reaction mixture was left stirring overnight at room temperature, evaporated down to 10 ml, and acidified to pH 1 with 1 N HCl. The product was extracted with methylene chloride (2×20 mL) and dried (MgSO$_4$), and the solvent evaporated under reduced pressure. The crude material was chromatographed on silica gel (eluting with chloroform: methanol). 1H NMR (CDC13) δ0.911 (t, 3H), 1.302 (d, 20 H), 1.597-1.612 (m, 5H), 2.054 (m, 4H), 2.283 (t, 2H), 3.860 (dd, 1H), 4.11 (dd, 1H), 4.503 (t, 1H), 5.37 (m, 2H).

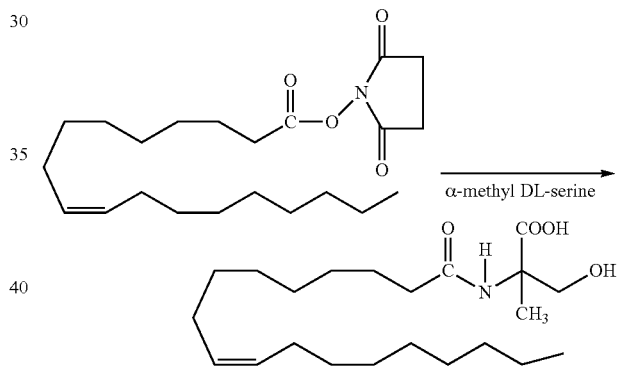

Example 2. Magel2 Mice as a Model of PWS in Humans

Among the different gene mutations involved in PWS that have been engineered in mice, only Magel2 mice recapitulate some of the metabolic and hormonal aspects of humans with PWS. The Magel2 gene is located 41 kn telomeric to Ndn, within the PWS region and its encoded protein acts as an adaptor protein for complexes that participate in signal transduction (Barker and Salehi, 2002). Magel2 mice have been widely used as an animal model of PWS to investigate metabolic, endocrine, and reproductive alterations as well as changes in the regulation of circadian rhythm characteristics of PWS (Devos et al., 2011; Kozlov et al., 2007; Mercer et al., 2013; Mercer and Wevirck, 2009; Meziane et al., 2015; Pravdivyi et al., 2015; Tennese and Wevrick, 2011).

FIG. 1 shows that female Magel2 mice have a low bone mass phenotype and shorter femora in comparison with their wild-type control. This phenotype results from reduced trabecular number (Tb.N), trabecular connective density (Conn.D) and cortical thickness (Cort.Th) and increased trabecular spacing.

Example 3. Administering HU-671 to Magel2 Mice to Prevent Bone Loss

The effect of HU-671 on preventing bone loss in female Magel2 mice and their littermates as controls was tested. Forty (40) 6-week old female mice were treated daily with HU-671 (0.5 mg/kg, IP) for a period of 6 weeks. Twenty-four (24) hours following the last administration of HU-671, a complete structural analysis of the trabecular and cortical bone in the distal femoral metaphysis was performed. The femora were fixed in phosphate buffered formalin for 48 hours and further kept at 70% ethanol. They were examined by a micro computed tomography (μCT) system. Scans were performed at 20-μm resolution in all three spatial dimensions. The mineralized tissues were differentially segmented by a global thresholding procedure.

Figure 2:
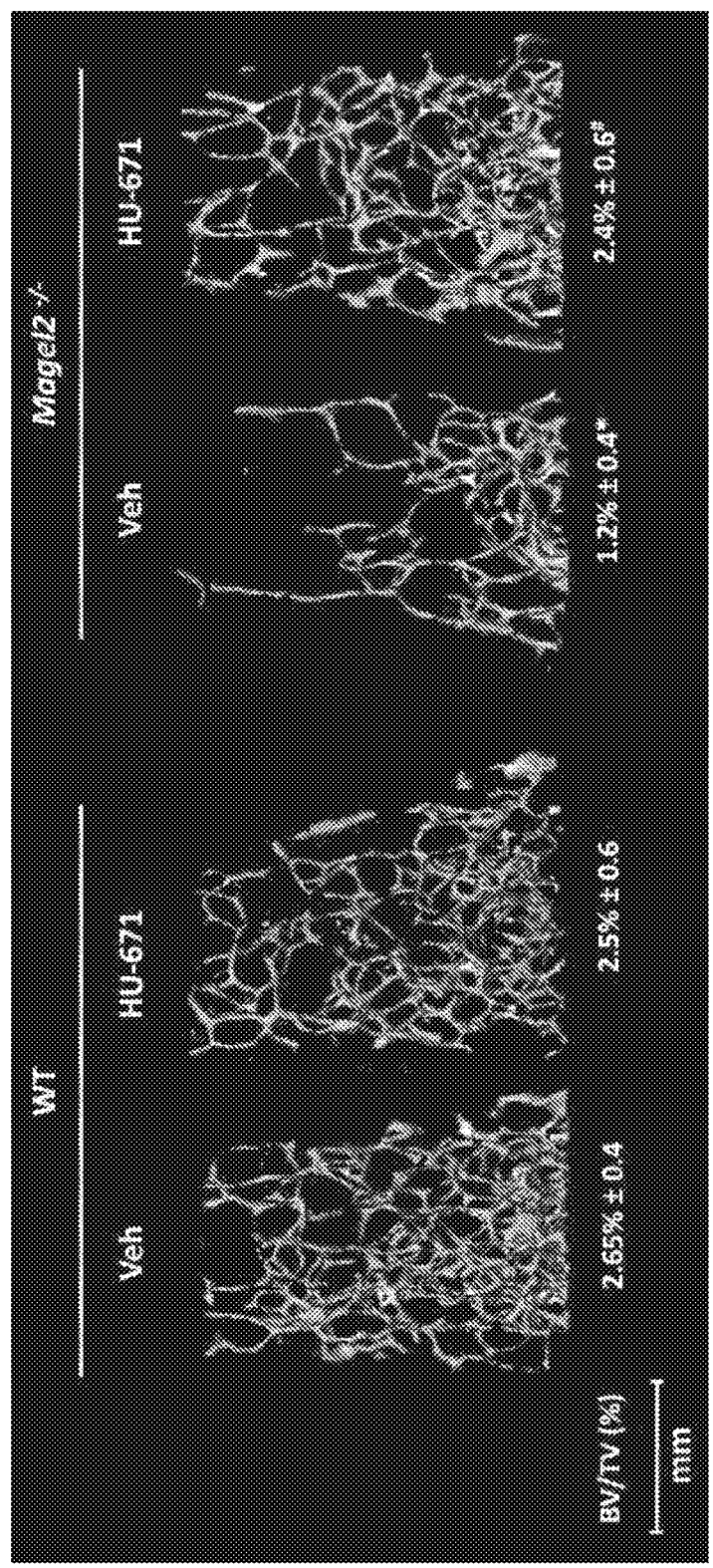
FIG. 2 shows that the reduced trabecular bone observed in 12-week old female Magel2-null mice is completely prevented in mice treated with HU-671 (0.5 mg/kg, IP for 6 weeks). Data are mean±SEM from 9-10 animals per group. *P<0.05 vs. wild-type littermate controls treated with vehicle (Veh), #P<0.05 vs. wild-type littermate controls treated with Veh.
Figure 3A:
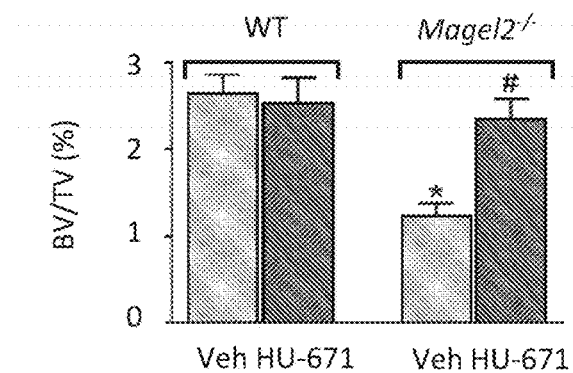
FIGS. 3A-3D show that the increase in trabecular bone mass observed in 12-week old female Magel2-null mice treated with HU-671 (0.5 mg/kg, IP for 6 weeks) results from increases in the BV/TV (1A), Tv.N (1B), TB.Th (1C) and Conn.D (1D). Data are mean±SEM from 9-10 animals per group. *P<0.05 vs. wild-type (WT) littermate controls treated with vehicle (Veh), #P<0.05 vs. Magel2-null mice treated with Veh.
Figure 3B:
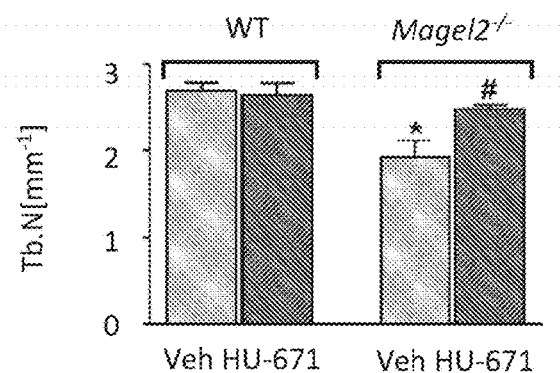
Figure 3C:
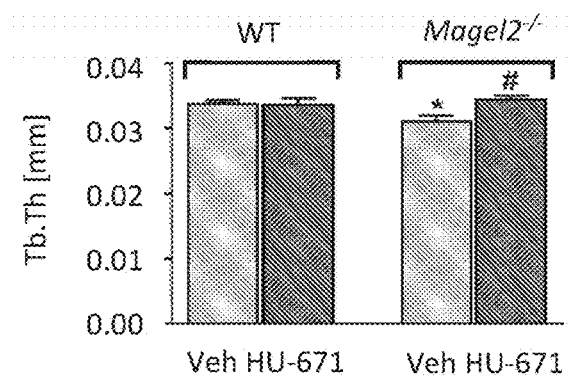
Figure 3D:
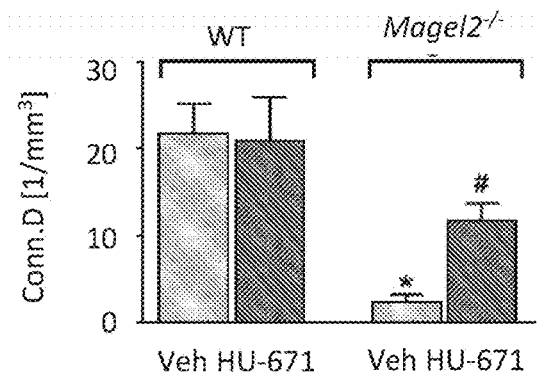

FIG. 2 demonstrates that HU-671 completely prevented the trabecular bone loss observed in vehicle-treated Magel2-null mice. FIGS. 2 and 3 show that HU-671 stimulated increase in bone volume density (BV/TV). This occurred mainly by increasing Tb.N and enhancing the Tb.Th. Importantly, the connectivity density in the trabecular bone was also significantly rescued by HU-671, which is shown in FIG. 3.

Figure 4:
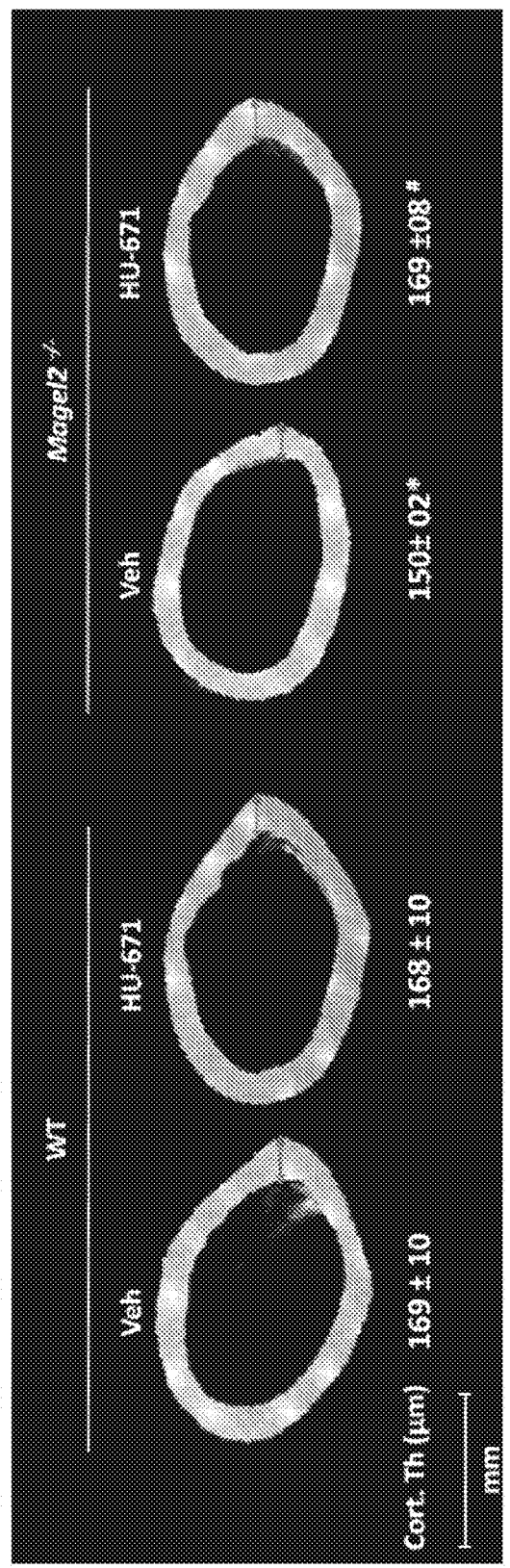
FIG. 4 shows that the reduced cortical thickness (Cort. Th) observed in 12-week old female Magel2-null mice is completely prevented in mice treated with HU-671 (0.5 mg/kg, IP for 6 weeks). Data are mean±SEM from 9-10 animals per group. *P<0.05 vs. wild-type (WT) littermate controls treated with vehicle (Veh), #P<0.05 vs. Magel2-null mice treated with Veh.

The rescue of PWS-induced bone loss by HU-671 was not selective only for the trabecular bone compartment. As can be seen in FIG. 4, the cortical parameters were also improved by HU-671. Chronic treatment with HU-671 was able to completely prevent the reduction in Cort.Th.

As demonstrated by the test results provided herein, administration of HU-671 to Magel2 mice has the ability to prevent bone loss. Thus, HU-671 can be used to treat and/or prevent human genetic syndromes associated with reduced BMD, such as PWS.

REFERENCES

Bakker N E; Kuppens R J; Siemensma E P; Tummers-de Lind van Wijngaarden R F; Festen D A; Bindels-de Heus G C; Bocca G; et al., Bone mineral density in children and adolescents with Prader-Willi syndrome: a longitudinal study during puberty and 9 years of growth hormone treatment. *J Clin Endocrinol Metab* 2015, 100, 1609-1618

Barker P A; Salehi A, The MAGE proteins: emerging roles in cell cycle progression, apoptosis, and neurogenetic disease. *J Neurosci Res* 2002, 67, 705-712

Butler M G; Haber L; Mernaugh R; Carlson M G; Price R; Feurer I D, Decreased bone mineral density in Prader-Willi syndrome: comparison with obese subjects. *Am J Med Genet* 2001, 103, 216-222

Carrel A L; Myers S E; Whitman B Y; Eickhoff J; Allen D B, Long-term growth hormone therapy changes the natural history of body composition and motor function in children with Prader-Willi syndrome. *J Clin Endocrinol Metab* 2010, 95, 1131-1136 de Lind van Wijngaarden R F; Festen D A; Otten B J; van Mil E G; Rotteveel J; Odink R J; van Leeuwen M; et al., Bone mineral density and effects of growth hormone treatment in prepubertal children with Prader-Willi syndrome: a randomized controlled trial. *J Clin Endocrinol Metab* 2009, 94, 3763-3771

Devos J; Weselake S V; Wevrick R, Magel2, a Prader-Willi syndrome candidate gene, modulates the activities of circadian rhythm proteins in cultured cells. *J Circadian Rhythms* 2011, 9, 12

Holm V A; Laurnen E L, Prader-Willi syndrome and scoliosis. *Dev Med Child Neurol* 1981, 23, 192-201

Kido Y; Sakazume S; Abe Y; Oto Y; Itabashi H; Shiraishi M; Yoshino A; et al., Testosterone replacement therapy to improve secondary sexual characteristics and body composition without adverse behavioral problems in adult male patients with Prader-Willi syndrome: an observational study. *Am J Med Genet A* 2013, 161A, 2167-2173

Kozlov S V; Bogenpohl J W; Howell M P; Wevrick R; Panda S; Hogenesch J B; Muglia L J; et al., The imprinted gene Magel2 regulates normal circadian output. *Nat Genet* 2007, 39, 1266-1272

Kroonen L T; Herman M; Pizzutillo P D; Macewen G D, Prader-Willi syndrome: clinical concerns for the orthopaedic surgeon. *J Pediatr Orthop* 2006, 26, 673-679 4

Lindmark M; Trygg K; Giltvedt K; Kolset S O, Nutritient intake of young children with Prader-Willi syndrome. *Food Nutr Res* 2010, 54

Mercer R E; Wevrick R, Loss of Magel2, a candidate gene for features of Prader-Willi syndrome, impairs reproductive function in mice. *PLoS One* 2009, 4, e4291

Mercer R E; Michaelson S D; Chee M J; Atallah T A; Wevrick R; Colmers W F, Magel2 is required for leptin-mediated depolarization of POMC neurons in the hypothalamic arcuate nucleus in mice. *PLoS Genet* 2013, 9, e1003207

Meziane H; Schaller F; Bauer S; Villard C; Matarazzo V; Riet F; Guillon G; et al., An early postnatal oxytocin treatment prevents social and learning deficits in adult mice deficient for Magel2, a gene involved in Prader-Willi syndrome and autism. *Biol Psychiatry* 2015, 78, 85-94

Pravdivyi I; Ballanyi K; Colmers W F; Wevrick R, Progressive postnatal decline in leptin sensitivity of arcuate hypothalamic neurons in the Magel2-null mouse model of Prader-Willi syndrome. *Hum Mol Genet* 2015, 24, 4276-4283

Tennese A A; Wevrick R, Impaired hypothalamic regulation of endocrine function and delayed counterregulatory response to hypoglycemia in Magel2-null mice. *Endocrinology* 2011, 152, 967-978

Vestergaard P; Kristensen K; Bruun J M; Ostergaard J R; Heickendorff L; Mosekilde L; Richelsen B1 Reduced bone mineral density and increased bone turnover in Prader-Willi syndrome compared with controls matched for sex and body mass index—a cross-sectional study. *J Pediatr* 2004, 144, 614-619

West L A; Ballock R T, High incidence of hip dysplasia but not slipped capital femoral epiphysis in patients with Prader-Willi syndrome. *J Pediatr Orthop* 2004, 24, 565-567

What is claimed is:

1. A method for treating Prader-Willi syndrome (PWS)-induced bone loss in a pediatric subject, said method comprising administering to said subject a therapeutically effective amount of a fatty acid amide of an amino acid, or a stereoisomer or salt thereof, wherein said fatty acid amide of an amino acid is of the formula I:

$$R_6-\overset{O}{\underset{}{C}}-\underset{H}{N}-\overset{CH_2R_4}{\underset{R_5}{C}}-COOH \qquad I$$

or a stereoisomer or salt thereof,
wherein:
$R_4$ is —OH, —SH, phenyl, or hydroxyphenyl;
$R_5$ is H, $(C_1\text{-}C_6)$alkyl, or —OR$_3$;

$R_6$ is a group of the formula II:

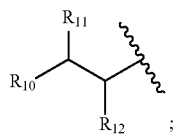

$R_{10}$ is $(C_{11}-C_{21})$alkyl, $(C_{11}-C_{21})$alkenyl, or $(C_{11}-C_{21})$alkynyl;

$R_{11}$ and $R_{12}$ each independently is H, $(C_1-C_6)$alkyl, $-OR_1$, or $-SR_2$; and $R_1$, $R_2$, and $R_3$ each independently is H or $(C_1-C_6)$alkyl, provided that at least one of $R_5$, $R_{11}$ and $R_{12}$ is not H.

2. The method of claim 1, wherein $R_4$ is $-OH$.

3. The method of claim 1, wherein $R_5$ is H or $(C_1-C_6)$alkyl.

4. The method of claim 3, wherein said $(C_1-C_6)$alkyl is methyl, ethyl, or isopropyl.

5. The method of claim 1, wherein $R_{10}$ is $(C_{11}-C_{21})$alkenyl.

6. The method of claim 5, wherein $R_{10}$ is $(C_{15})$alkenyl.

7. The method of claim 6, wherein $R_{10}$ is $-(CH_2)_5-CH=CH-(CH_2)_7-CH_3$.

8. The method of claim 1, wherein $R_{11}$ and $R_{12}$ each independently is H or $(C_1-C_6)$alkyl.

9. The method of claim 8, wherein said $(C_1-C_6)$alkyl is methyl, ethyl, or isopropyl.

10. The method of claim 1, wherein $R_4$ is $-OH$; $R_5$ is H or $(C_1-C_6)$alkyl; $R_{10}$ is $(C_{11}-C_{21})$alkenyl; and $R_{11}$ and $R_{12}$ each independently is H or $(C_1-C_6)$alkyl.

11. The method of claim 10, wherein $R_5$ is H, methyl, ethyl, or isopropyl; $R_{10}$ is $(C_{15})$alkenyl; and $R_{11}$ and $R_{12}$ each independently is H, methyl, ethyl, or isopropyl.

12. The method of claim 11, wherein $R_{10}$ is $-(CH_2)_5-CH=CH-(CH_2)_7-CH_3$.

13. The method of claim 12, wherein (i) $R_5$ is methyl, $R_{11}$ is H, and $R_{12}$ is H; (ii) $R_5$ is methyl, $R_{11}$ is H, and $R_{12}$ is methyl; (iii) $R_5$ is methyl, $R_{11}$ is methyl, and $R_{12}$ is H; (iv) $R_5$ is methyl, $R_{11}$ is methyl, and $R_{12}$ is methyl; (v) $R_5$ is H, $R_{11}$ is H, and $R_{12}$ is methyl; (vi) $R_5$ is H, $R_{11}$ is methyl, and $R_{12}$ is H; or (vi) $R_5$ is H, $R_{11}$ is methyl, and $R_{12}$ is methyl.

14. The method of claim 13, wherein $R_5$ is methyl, $R_{11}$ is H, and $R_{12}$ is H.

15. The method according to claim 1, further comprising administering an additional active agent.

16. The method according to claim 15, wherein said active agent is a bisphosphonate, hormone, anti-receptor activator of nuclear factor kappa-B ligand, cathepsin K inhibitor, or anti-sclerostin antibody.

* * * * *